(12) United States Patent
Valoti et al.

(10) Patent No.: US 8,258,115 B2
(45) Date of Patent: Sep. 4, 2012

(54) STABLE SALTS OF S-ADENOSYLMETHIONINE AND PROCESS FOR THE PREPARATION THEREOF

(75) Inventors: Ermanno Valoti, Dalmine (IT); Daniele Giovannone, Frosinone (IT); Marco Berna, Muggio (IT)

(73) Assignee: Gnosis SpA, Milan (IT)

( * ) Notice: Subject to any disclaimer, the term of this patent is extended or adjusted under 35 U.S.C. 154(b) by 374 days.

(21) Appl. No.: 12/665,808

(22) PCT Filed: Oct. 22, 2007

(86) PCT No.: PCT/IT2007/000736
§ 371 (c)(1),
(2), (4) Date: Feb. 8, 2010

(87) PCT Pub. No.: WO2009/008019
PCT Pub. Date: Jan. 15, 2009

(65) Prior Publication Data
US 2010/0184715 A1 Jul. 22, 2010

(30) Foreign Application Priority Data
Jul. 10, 2007 (IT) .............. MI2007A1374

(51) Int. Cl.
*A01N 43/04* (2006.01)
*A61K 31/70* (2006.01)
(52) U.S. Cl. ............. 514/46; 514/43; 514/45; 536/27.1; 536/27.13; 536/27.2; 536/27.21; 536/27.22; 536/27.23; 536/27.3; 536/27.31
(58) Field of Classification Search .................. None
See application file for complete search history.

(56) References Cited

U.S. PATENT DOCUMENTS

| | | | |
|---|---|---|---|
| 3,330,729 A | 7/1967 | Johnson, Jr. | |
| 3,893,999 A | 7/1975 | Fiecchi | |
| 3,954,726 A | 5/1976 | Fiecchi | |
| 4,057,686 A * | 11/1977 | Fiecchi | 536/27.31 |
| 4,369,177 A | 1/1983 | Kozaki | |
| 4,558,122 A | 12/1985 | Gennari | |
| 4,704,365 A | 11/1987 | Yost | |
| 4,935,246 A | 6/1990 | Ahrens | |
| 6,451,341 B1 | 9/2002 | Slaga et al. | |
| 2002/0010147 A1 | 1/2002 | Berna et al. | |
| 2002/0132780 A1 | 9/2002 | Heisey et al. | |
| 2002/0164369 A1 | 11/2002 | Rao | |
| 2004/0209841 A1 | 10/2004 | Oku et al. | |
| 2005/0090512 A1 | 4/2005 | Geiss et al. | |

FOREIGN PATENT DOCUMENTS

| | | |
|---|---|---|
| AU | 4734993 | 3/1994 |
| DE | 3721721 | 6/1988 |
| EP | 0009222 | 4/1980 |
| EP | 0253684 | 1/1988 |
| EP | 0421581 | 4/1991 |
| EP | 0588707 | 3/1994 |
| JP | 60181095 A | 9/1985 |
| WO | 9425007 A1 | 11/1994 |
| WO | 0018259 A1 | 4/2000 |
| WO | 0193847 | 12/2001 |
| WO | WO02/102823 | 12/2002 |
| WO | 03043608 | 5/2003 |
| WO | WO2007/004244 | 1/2007 |

OTHER PUBLICATIONS

International Search Report for PCT/IT2007/000736.
Written Opinion of the International Searching Authority RE PCT/IT2007/000736.
International Search Report for PCT/EP2006/060761, dated Aug. 2, 2007.
Pursuant to MPEP 1002.6(B), applicants bring the following co-pending application to the Examiner's Attention: U.S. Appl. No. 12/240,002, filed Sep. 29, 2008.
International Search Report for PCT/IT2006/000610, dated Jan. 24, 2008.
Written Opinion for PCT/IT2006/000610, dated Jan. 24, 2008.
International Search Report for PCT/IT2007/000736, dated Aug. 6, 2008.
Written Opinion of the International Searching Authority RE PCT/IT2007/000736, dated Aug. 6, 2008.
Birkmayer, J. G. D. et al: "Safety of stabilized, orally absorbable, reduced nicotinamide adenine dinucleotide (NADH): A 26-week oral table administration of ENADA/NADH for chronic toxicity study in rats", Drugs Under Experimental and Clinical Research 2002, vol. 28, No. 5.
Office Action date Apr. 29, 2010, Applicant's co-pending U.S. Appl. No. 12/240,002.

* cited by examiner

*Primary Examiner* — Patrick Lewis
(74) *Attorney, Agent, or Firm* — Scott D. Swanson; Dykas & Shaver, LLP

(57) ABSTRACT

The present invention refers to new salts of S-adenosykneth-ionine (SAMe) with improved stability and containing at least 70% by weight of SAMe.

22 Claims, No Drawings

STABLE SALTS OF S-ADENOSYLMETHIONINE AND PROCESS FOR THE PREPARATION THEREOF

S-adenosylmethionine (SAMe) is physiological donor of methyl groups present in every living organism and employed in enzymatic transmethylation reactions.

Such substance therefore has a role of considerable biological importance, and is essentially clinically used as an anti-depressive.

By "SAMe", it is intended to indicate both the racemic mixture and the single diastereoisomers (RS)-(+)-S-adenosyl-L-methionine [(RS)-(+)-SAMe)] and (SS)-(+)-S-adenosyl-L-methionine [(SS)-(+)-SAMe)], also in mixtures different from the racemic mixture.

The difficulty of using S-adenosylmethionine as drug and/or dietetic product is however known, since it is extremely unstable at temperatures above 0° C. or in the presence of moisture, both as degradation of the active ingredient intended as the sum of the two diastereoisomers and as transformation of active (SS)-(+)-S-adenosyl-L-methionine into inactivate (RS)-(+)-S-adenosyl-L-methionine (racemisation of the substance).

SAMe corresponds to the following formula:

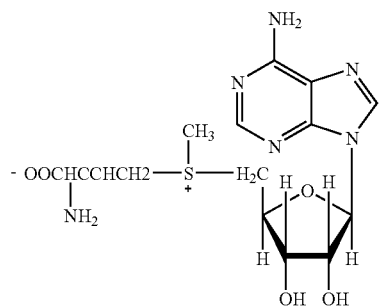

SAMe participates in a great number of metabolic processes of fundamental importance for the human body, and its deficiency therefore underlies many organic malfunctions.

Even if the biological importance of this product has been known for a long time, the possibility to examine and use it as a drug and/or dietetic product has only developed recently, above all due to its extreme instability at temperatures above 0° C.

Only in 1975 was a sufficiently stable SAMe salt successively prepared at 25° C. (U.S. Pat. No. 3,893,999), followed afterward by other salts with good stability also at 45° C. (U.S. Pat. No. 3,954,726 and U.S. Pat. No. 4,057,686).

More specifically, U.S. Pat. No. 3,893,999 describes tri-p-toluensulphonate of SAMe, U.S. Pat. No. 3,954,726 describes disulphate di-p-toluensulphonate of SAMe, U.S. Pat. No. 4,057,686 describes a group of SAMe salts which can be indicated overall as SAMe.4RSO$_3$H or SAMe 3RSO$_3$H in which the RSO$_3$H indicates a disulphonic acid equivalent which can partly substitute the equivalents of sulphuric acid.

The US patent application No. 20020010147 describes a process for preparing salts of (SS,RS)-SAM in which the salified diastereoisomer RS(+) SAMe is present in a much lower amount than the salified diastereoisomer SS(+) SAMe.

It has now been surprisingly found that salts of SAMe having an improved stability over time are obtained by salifying the SAMe with 0.5-2.0 moles/mole of a strong inorganic acid with an acid dissociation constant (pKa) of less than 2.5 added with 0.5-1.0 moles/mole of an oxide and/or salt. Said oxide and/or salt is preferably selected from among calcium oxide, magnesium oxide, calcium chloride, magnesium chloride, calcium sulphate, magnesium sulphate and/or a mixture thereof.

Said salts of SAMe according to the present invention preferably contain a high percentage of SAMe. More preferably, the percentage of SAMe in the aforesaid salts is at least 70% by weight, and still more preferably is in the range of 75-90%.

Salts of SAMe that contain lesser quantities of acid, oxide and/or salt are unacceptable for therapeutic use, since they are subject to degradation phenomena. It has in fact been noted how the presence even of small percentages of degradation products is unacceptable, not only since it leads to the loss of activity, but also and above all since it causes the formation of metabolites which have resulted to be toxic. The object of the present invention are therefore SAMe salts having the following general formula (I).

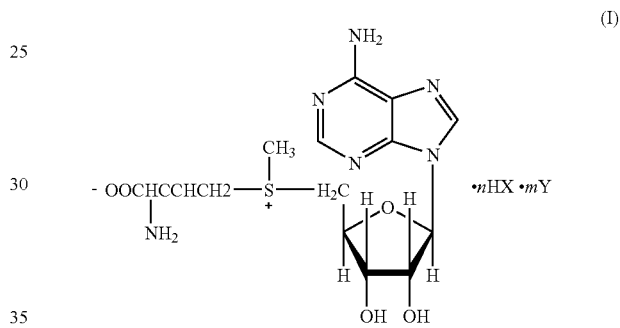

where

HX is a strong mineral acid having an acid dissociation constant (pKa) of less than 2.5;

n and m are independently in the range of 0.5-2.0;

Y is a calcium oxide, magnesium oxide, calcium chloride, magnesium chloride, calcium sulphate, magnesium sulphate and/or a mixture thereof;

Preferably, HX is an acid selected from among hydrochloric acid, sulphuric acid, phosphoric acid, phosphorous acid, disulphonic acid and/or 1,4 butanedisulphonic acid.

Examples of SAMe salts according to the present invention preferably correspond to the following general formulas (II) and (III):

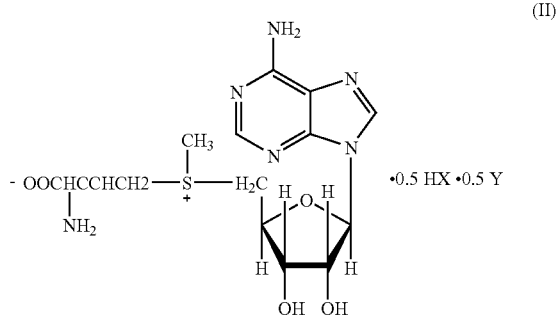

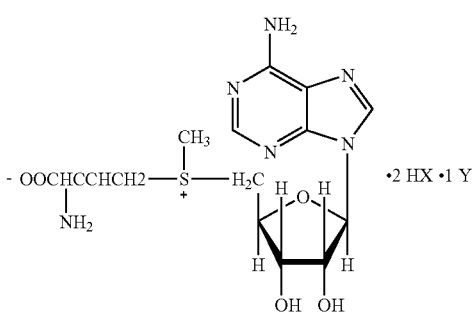

where
HX is a strong mineral acid having acid dissociation constant (pKa) of less than 2.5;
Y is calcium oxide, magnesium oxide, calcium chloride, magnesium chloride, calcium sulphate, magnesium sulphate and/or a mixture thereof.

Preferably, HX is an acid selected from among hydrochloric acid, sulphuric acid, phosphoric acid, phosphorous acid, disulphonic acid and/or 1,4 butanedisulphonic acid.

According to the present invention, the pKa of the aforesaid acids correspond to the following values:
HCl pKa<0.5; $H_2SO_4$ $pKa_1$<0.5, $pKa_2$=1.92 (2° ionisation or dissociation constant); $H_3PO_4$ $pKa_1$<0.5, $pKa_2$=2.12 (2° ionisation or dissociation constant), $pKa_3$=2.3 (3° ionisation or dissociation constant).

The improved stability of the salts of SAMe of the present invention is also directly correlated with the size and shape of the product itself in drying phase. This because the shape and size of the final powder influence the hygroscopicity of the product, which determines the stability of the same to the extent that the closer the hygroscopicity value approaches zero, the greater the stability of the salt of SAMe.

In particular, the particle sizes of the salt according to the present invention are preferably in the range of 20-500 µm, more preferably in the range of 50-300 µm, and the particles are preferably in oval or spherical form, more preferably spherical. The drying phase of the product according to the present invention occurs through a lyophilisation passage, preceded by a freezing passage by ultrasonic spray cooling. Said freezing is preferably carried out according to the method described in U.S. Pat. No. 707,636.

The salts of SAMe according to the present invention moreover contain a high percentage of the active diastereoisomer, (SS)-(+)-S-adenosyl-L-methionine, of the SAMe.

Said percentage of (SS)-(+)-S-adenosyl-L-methionine is preferably at least 80% by weight, more preferably in the range of 85-95% calculated with respect to the sum of the two diastereoisomers.

A further object of the invention is the use of at least of the salts of formula (I)

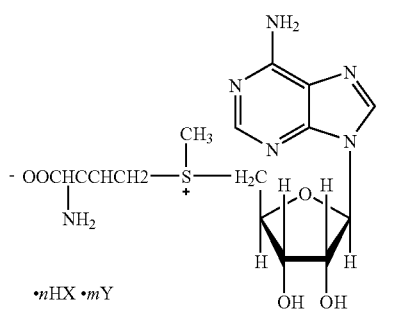

HX is a strong mineral acid having an acid dissociation constant (pKa) of less than 2.5;

n and m are independently in the range of 0.5-2.0;

Y is a calcium oxide, magnesium oxide, calcium chloride, magnesium chloride, calcium sulphate, magnesium sulphate and/or a mixture thereof for the preparation of a medicament for the treatment of depressive states.

Preferably, HX is an acid selected from among hydrochloric acid, sulphuric acid, phosphoric acid, phosphorous acid, disulphonic acid and/or 1,4 butanedisulphonic acid.

The following examples are present in order to better understand the invention, without in any manner limiting it.

EXAMPLES

Example 1

In two 100 mL aliquots of distilled water, 40 grams of SAMe were dissolved containing respectively 0.5 or 2.0 moles of sulphuric acid.

The obtained solutions were altered on 0.20 µm filters up to complete transparency. To the aqueous solutions thus prepared, 0.5 or 1.0 moles of magnesium oxide were respectively added and once again filtered on a 0.20 µm filter.

The two salts thus prepared were subjected to quick freezing with the spray cooling method and subsequently subjected to lyophilisation.

In such a manner, two products were obtained with the following compositions: SAMe.0.5$H_2SO_4$.0.5$Mg_2SO_4$.0.4$H_2O$ and SAMe.2.0$H_2SO_4$.1.0$Mg_2SO_4$.0.4$H_2O$.

The salts have a white crystalline aspect with granulometry in the range of 50-300 µm and perfectly spherical form. They are extremely soluble in water up to about 60 mg/mL.

The high-resolution, thin-layer chromatography shows that the product is free of any impurity.

Table 1 reports the analytic data of the aforesaid two salts.

Example 2

Two aqueous solutions containing SAMe and sulphuric acid were prepared according to the method described in Example 1.

To the aqueous solutions thus prepared, 0.5 or 1.0 moles of magnesium chloride were respectively added and once again filtered on a 0.20 µm filter.

The two salts thus prepared were subjected to quick freezing with the spray cooling method and subsequent lyophilisation as in example 1.

In such a manner, six products were obtained with the following compositions: SAMe.0.5$H_2SO_4$.0.5$MgCl_2$.0.4$H_2O$ and SAMe.2.0$H_2SO_4$.1.0$MgCl_2$.0.4$H_2O$.

The salts have a white crystalline aspect with granulometry in the range of 50-300 µm and perfectly spherical form. They are extremely soluble in water up to about 60 mg/mL.

The high-resolution, thin-layer chromatography shows that the product is free of any impurity.

Table 1 reports the analytic data of the aforesaid two salts.

Example 3

Two aqueous solutions containing SAMe and sulphuric acid are prepared according to the method described in Example 1.

To the aqueous solutions thus prepared, 0.5 or 1.0 moles of $CaCl_2$ were respectively added and once again filtered on a 0.20 μm filter.

The solution was then frozen and lyophilised by spray cooling and subsequently subjected to lyophilisation.

In such a manner, six products were obtained with the following compositions: SAMe.0.5H2SO4.0.5CaCl2.0.4H2O and: SAMe.2.0H2SO4.1.0CaCl2.0.4H2O.

The salts have a white crystalline aspect with granulometry in the range of 50-300 μm and perfectly spherical form. They are extremely soluble in water up to about 60 mg/mL.

The high-resolution, thin-layer chromatography shows that the product is free of any impurity.

Table 1 reports the analytic data of the aforesaid two salts.

Example 4

In two 100 mL aliquots of distilled water, 40 grams of SAMe were dissolved containing respectively 0.5 or 2.0 moles of hydrochloric acid.

The obtained solutions were filtered on 0.20 μm filters up to complete transparency. To the aqueous solutions thus prepared, 0.5 or 1.0 moles of magnesium sulphate were respectively added and once again filtered on a 0.20 μm filter.

The two salts thus prepared were subjected to quick freezing by spray cooling and subsequent lyophilisation.

In such a manner, two products were obtained with the following compositions: SAMe.0.5 HCl.0.5Mg2SO4.0.4H2O and SAMe.2.0HCl.1.0Mg2SO4.0.4H2O.

The salts have a white crystalline aspect with granulometry in the range of 50-300 μm and perfectly spherical form. They are extremely soluble in water up to about 60 mg/mL.

The high-resolution, thin-layer chromatography shows that the product is free of any impurity.

Table 1 reports the analytic data of the aforesaid two salts.

Example 5

Two aqueous solutions containing SAMe and sulphuric acid are prepared according to the method described in Example 4.

To the aqueous solutions thus prepared, 0.5 or 1.0 moles of magnesium chloride were added and once again filtered on a 0.20 μm filter.

The solution was then frozen and lyophilised by spray cooling and subsequently lyophilised.

In such a manner, six products were obtained with the following compositions: SAMe.0.5HCl.0.5MgCl2.0.4H2O and SAMe.2.0HCl.1.0 MgCl2.0.4H2O.

The salts have a white crystalline aspect with granulometry in the range of 50-300 μm and perfectly spherical form. They are extremely soluble in water up to about 60 mg/mL.

The high-resolution, thin-layer chromatography shows that the product is free of any impurity.

Table 1 reports the analytic data of the aforesaid two salts.

Example 6

Two aqueous solutions containing SAMe and sulphuric acid are prepared according to the method described in Example 4.

To the aqueous solutions thus prepared, 0.5 or 1.0 moles of calcium chloride are added and once again filtered on a 0.20 μm filter.

The solution was frozen and lyophilised by spray cooling and subsequently lyophilised.

In such a manner, six products were obtained with the following compositions: SAMe.0.5HCl.0.5 CaCl2.0.4H2O and SAMe.2.0HCl.1.0 CaCl2.0.4H2O. The salts have a white crystalline aspect with granulometry in the range of 50-300 μm and perfectly spherical form. They are extremely soluble in water up to about 60 mg/mL.

The high-resolution, thin-layer chromatography shows that the product is free of any impurity.

Table 1 reports the analytic data of the aforesaid two salts.

TABLE 1

| Salt of SAMe | Example | % SAMe | % Acid | % Oxide/Salt |
|---|---|---|---|---|
| SAMe•0.5H2SO4•0.5MgSO4•0.4 H2O | Ex. 1 | 78.6 | 9.7 | 11.7 |
| SAMe•2.0H2SO4•1.0MgSO4•0.4 H2O | Ex. 1 | 56.0 | 27.4 | 16.6 |
| SAMe•0.5H2SO4•0.5MgCl•0.4 H2O | Ex. 2 | 80.5 | 9.9 | 9.6 |
| SAMe•2.0H2SO4•1.0MgCl2•0.4 H2O | Ex. 2 | 57.7 | 28.5 | 13.7 |
| SAMe•0.5H2SO4•0.5CaCl2•0.4 H2O | Ex. 3 | 71.2 | 8.8 | 20.0 |
| SAMe•2.0H2SO4•1.0CaCl2•0.4 H2O | Ex. 3 | 56.4 | 27.9 | 15.7 |
| SAMe•0.5HCl•0.5MgSO4•0.4 H2O | Ex. 4 | 83.6 | 3.9 | 12.5 |
| SAMe•2.0HCl•1.0MgSO4•0.4 H2O | Ex. 4 | 75.0 | 13.9 | 11.9 |
| SAMe•0.5HCl•0.5MgCl2•0.4 H2O | Ex. 5 | 85.8 | 4.0 | 10.2 |
| SAMe•2.0HCl•1.0MgCl2•0.4 H2O | Ex. 5 | 70.3 | 13.0 | 16.7 |
| SAMe•0.5HCl•0.5CaCl2•0.4 H2O | Ex. 6 | 84.3 | 4.0 | 11.7 |
| SAMe•2.0HCl•1.0CaCl2•0.4 H2O | Ex. 6 | 68.2 | 12.6 | 19.2 |

In the following Tables 2-13, the percentage values are repotted which were obtained in the stability tests carried out on the products of examples 1-6. The stability tests were carried out in thermostated heaters at 40° C. and 75% R.H (tables 2-7) as well as 25° C. and 60% R.H. (tables 8-13), preserving the samples in heat-sealed aluminium/aluminium bags according to the following criteria:

the active ingredient % was determined for every sampling point taken under consideration.

TABLE 2

Example 1
SAMe•0.5H2SO4•0.5Mg2SO4•0.4H2O and
SAMe•2.0H2SO4•1.0Mg2SO4•0.4H2O.

| Moisture % K.F. | 30 days % | 60 days % | 90 days % | 120 days % | 180 days % |
|---|---|---|---|---|---|
| 0.57 | 0.57 | 0.65 | 0.96 | 1.40 | 2.18 |
| 0.34 | 0.33 | 0.44 | 0.61 | 1.02 | 1.59 |

TABLE 3

Example 2
SAMe•0.5H₂SO₄•0.5MgCl₂ and SAMe•2.0H₂SO₄•1.0MgCl₂

| Moisture % K.F. | 30 days % | 60 days % | 90 days % | 120 days % | 180 days % |
|---|---|---|---|---|---|
| 0.61 | 0.36 | 0.70 | 1.16 | 1.66 | 2.45 |
| 0.52 | 0.19 | 0.34 | 0.82 | 1.12 | 1.87 |

TABLE 4

Example 3
SAMe•0.5H₂SO₄•0.5CaCl₂ and SAMe•2.0H₂SO₄•1.0CaCl₂

| Moisture % K.F. | 30 days % | 60 days % | 90 days % | 120 days % | 180 days % |
|---|---|---|---|---|---|
| 0.23 | 0.48 | 0.76 | 1.48 | 1.98 | 3.99 |
| 0.35 | 0.17 | 0.42 | 0.92 | 1.52 | 2.70 |

TABLE 5

Example 4
SAMe•0.5HCl•0.5MgSO₄ and SAMe•2.0HCl•1.0MgSO₄

| Moisture % K.F. | 30 days % | 60 days % | 90 days % | 120 days % | 180 days % |
|---|---|---|---|---|---|
| 0.82 | 0.48 | 0.78 | 1.54 | 1.98 | 2.78 |
| 0.52 | 0.27 | 0.49 | 0.67 | 1.46 | 1.62 |

TABLE 6

Example 5
SAMe•0.5HCl•0.5MgCl₂ and SAMe•2.0HCl•1.0MgCl₂

| Moisture % K.F. | 30 days % | 60 days % | 90 days % | 120 days % | 180 days % |
|---|---|---|---|---|---|
| 0.54 | 0.56 | 0.87 | 1.45 | 1.99 | 2.67 |
| 0.44 | 0.27 | 0.45 | 1.14 | 1.45 | 1.89 |

TABLE 7

Example 6
SAMe•0.5HCl•2.0CaCl₂ and SAMe•2.0HCl•1.0CaCl₂

| Moisture % K.F. | 30 days % | 60 days % | 90 days % | 120 days % | 180 days % |
|---|---|---|---|---|---|
| 0.45 | 0.66 | 0.86 | 1.63 | 1.97 | 2.96 |
| 0.34 | 0.36 | 0.59 | 0.95 | 1.37 | 2.20 |

TABLE 8

Example 1
SAMe•0.5H₂SO₄•0.5Mg₂SO₄•0.4H₂O and
SAMe•2.0H₂SO₄•1.0Mg₂SO₄•0.4H2O.

| Moisture % K.F. | 30 days % | 90 days % | 180 days % | 360 days % | 720 days % |
|---|---|---|---|---|---|
| 0.57 | 0.23 | 0.45 | 0.65 | 0.87 | 0.99 |
| 0.34 | 0.14 | 0.28 | 0.45 | 0.69 | 0.92 |

TABLE 9

Example 2
SAMe•0.5H₂SO₄•0.5MgCl₂ and SAMe•2.0H₂SO₄•1.0MgCl₂

| Moisture % K.F. | 30 days % | 90 days % | 180 days % | 360 days % | 720 days % |
|---|---|---|---|---|---|
| 0.61 | 0.12 | 0.25 | 0.35 | 0.57 | 0.79 |
| 0.52 | 0.10 | 0.18 | 0.25 | 0.49 | 0.62 |

TABLE 10

Example 3
SAMe•0.5H₂SO₄•0.5CaCl₂ and SAMe•2.0H₂SO₄•1.0CaCl₂

| Moisture % K.F. | 30 days % | 90 days % | 180 days % | 360 days % | 720 days % |
|---|---|---|---|---|---|
| 0.23 | 0.23 | 0.35 | 0.57 | 0.78 | 0.99 |
| 0.35 | 0.16 | 0.29 | 0.35 | 0.68 | 0.82 |

TABLE 11

Example 4
SAMe•0.5HCl•0.5MgSO₄ and SAMe•2.0HCl•1.0MgSO₄

| Moisture % K.F. | 30 days % | 90 days % | 180 days % | 360 days % | 720 days % |
|---|---|---|---|---|---|
| 0.82 | 0.31 | 0.46 | 0.77 | 0.94 | 1.19 |
| 0.52 | 0.19 | 0.28 | 0.41 | 0.65 | 0.87 |

TABLE 12

Example 5
SAMe•0.5HCl•0.5MgCl₂ and SAMe•2.0HCl•1.0MgCl₂

| Moisture % K.F. | 30 days % | 90 days % | 180 days % | 360 days % | 720 days % |
|---|---|---|---|---|---|
| 0.54 | 0.35 | 0.43 | 0.76 | 0.90 | 1.07 |
| 0.44 | 0.17 | 0.37 | 0.58 | 0.74 | 0.98 |

TABLE 13

Example 6
SAMe•0.5HCl•2.0CaCl₂ and SAMe•2.0HCl•1.0CaCl₂

| Moisture % K.F. | 30 days % | 90 days % | 180 days % | 360 days % | 720 days % |
|---|---|---|---|---|---|
| 0.45 | 0.21 | 0.42 | 0.67 | 0.84 | 1.06 |
| 0.34 | 0.13 | 0.25 | 0.48 | 0.64 | 0.97 |

In the following Tables 14-25, the percentage values are reported of the degradation of the active stereoisomer S,S calculated at 40° C. and 75% R.H. (Tables 14-19) and at 25° C. and 65% R.H.

TABLE 14

Example 1
SAMe•0.5H₂SO₄•0.5Mg₂SO₄•0.4H₂O and
SAMe•2.0H₂SO₄•1.0Mg₂SO₄•0.4H2O.

| T = 0 | 30 days % | 60 days % | 90 days % | 120 days % | 180 days % |
|---|---|---|---|---|---|
| 98.2 | 90.8 | 88.8 | 85.6 | 82.6 | 78.6 |
| 97.5 | 91.3 | 89.4 | 84.1 | 81.3 | 75.8 |

TABLE 15

Example 2
SAM•0.5H$_2$SO$_4$•0.5MgCl$_2$ and SAMe•2.0H$_2$SO$_4$•1.0MgCl$_2$

| T = 0 | 30 days % | 60 days % | 90 days % | 120 days % | 180 days % |
|---|---|---|---|---|---|
| 98.2 | 89.8 | 86.8 | 83.6 | 80.6 | 77.6 |
| 97.2 | 89.3 | 85.3 | 83.3 | 89.3 | 75.3 |

TABLE 16

Example 3
SAMe•0.5H$_2$SO$_4$•0.5CaCl$_2$ and SAMe•2.0H$_2$SO$_4$•1.0CaCl$_2$

| T = 0 | 30 days % | 60 days % | 90 days % | 120 days % | 180 days % |
|---|---|---|---|---|---|
| 98.2 | 89.8 | 86.8 | 83.6 | 80.6 | 77.6 |
| 97.2 | 89.3 | 85.3 | 83.3 | 79.3 | 75.3 |

TABLE 17

Example 4
SAMe•0.5HCl•0.5MgSO$_4$ and SAMe•2.0HCl•1.0MgSO$_4$

| T = 0 | 30 days % | 60 days % | 90 days % | 120 days % | 180 days % |
|---|---|---|---|---|---|
| 98.9 | 92.8 | 87.8 | 84.6 | 89.6 | 72.6 |
| 98.0 | 89.9 | 87.9 | 83.0 | 79.1 | 73.3 |

TABLE 18

Example 5
SAMe•0.5HCl•0.5MgCl$_2$ and SAMe•2.0HCl•1.0MgCl$_2$

| T = 0 | 30 days % | 60 days % | 90 days % | 120 days % | 180 days % |
|---|---|---|---|---|---|
| 98.9 | 92.5 | 89.8 | 84.5 | 82.6 | 76.6 |
| 97.4 | 92.9 | 87.8 | 83.4 | 82.1 | 78.2 |

TABLE 19

Example 6
SAMe•0.5HCl•2.0CaCl$_2$ and SAMe•2.0HCl•1.0CaCl$_2$

| T = 0 | 30 days % | 60 days % | 90 days % | 120 days % | 180 days % |
|---|---|---|---|---|---|
| 97.6 | 92.3 | 91.8 | 85.4 | 83.6 | 80.6 |
| 97.9 | 92.3 | 88.9 | 85.4 | 82.5 | 79.2 |

TABLE 20

Example 1
SAMe•0.5H$_2$SO$_4$•0.5Mg$_2$SO$_4$•0.4H$_2$O and
SAMe•2.0H$_2$SO$_4$•1.0Mg$_2$SO$_4$•0.4H$_2$

| T = 0 | 30 days % | 90 days % | 180 days % | 360 days % | 720 days % |
|---|---|---|---|---|---|
| 98.2 | 97.8 | 96.8 | 95.6 | 92.6 | 88.6 |
| 97.5 | 97.3 | 96.4 | 94.1 | 91.3 | 89.8 |

TABLE 21

Example 2
SAMe•0.5H$_2$SO$_4$•0.5MgCl$_2$ and SAMe•2.0H$_2$SO$_4$•1.0MgCl$_2$

| T = 0 | 30 days % | 90 days % | 180 days % | 360 days % | 720 days % |
|---|---|---|---|---|---|
| 98.2 | 97.8 | 96.8 | 93.6 | 90.6 | 87.6 |
| 97.2 | 96.3 | 95.3 | 93.3 | 91.0 | 88.0 |

TABLE 22

Example 3
SAMe•0.5H$_2$SO$_4$•0.5CaCl$_2$ and SAMe•2.0H$_2$SO$_4$•1.0CaCl$_2$

| T = 0 | 30 days % | 90 days % | 180 days % | 360 days % | 720 days % |
|---|---|---|---|---|---|
| 98.2 | 97.8 | 96.7 | 93.6 | 90.8 | 88.6 |
| 97.2 | 95.9 | 94.9 | 93.8 | 91.2 | 87.8 |

TABLE 23

Example 4
SAMe•0.5HCl•0.5MgSO$_4$ and SAMe•2.0HCl•1.0MgSO$_4$

| T = 0 | 30 days % | 90 days % | 180 days % | 360 days % | 720 days % |
|---|---|---|---|---|---|
| 98.9 | 97.8 | 95.8 | 94.3 | 91.6 | 88.2 |
| 98.0 | 86.5 | 95.6 | 93.0 | 91.1 | 88.2 |

TABLE 24

Example 5
SAMe•0.5HCl•0.5MgCl$_2$ and SAMe•2.0HCl•1.0MgCl$_2$

| T = 0 | 30 days % | 90 days % | 180 days % | 360 days % | 720 days % |
|---|---|---|---|---|---|
| 98.9 | 96.5 | 94.8 | 93.7 | 92.6 | 89.5 |
| 97.4 | 96.6 | 95.7 | 94.7 | 92.5 | 88.0 |

TABLE 25

Example 6
SAMe•0.5HCl•2.0CaCl$_2$ and SAMe•2.0HCl•1.0CaCl$_2$

| T = 0 | 30 days % | 90 days % | 180 days % | 360 days % | 720 days % |
|---|---|---|---|---|---|
| 97.6 | 96.3 | 95.5 | 94.4 | 93.1 | 91.6 |
| 97.9 | 96.3 | 95.4 | 94.2 | 92.6 | 89.8 |

The invention claimed is:

1. Salt of S-adenosylmethionine (SAMe) of formula (I):

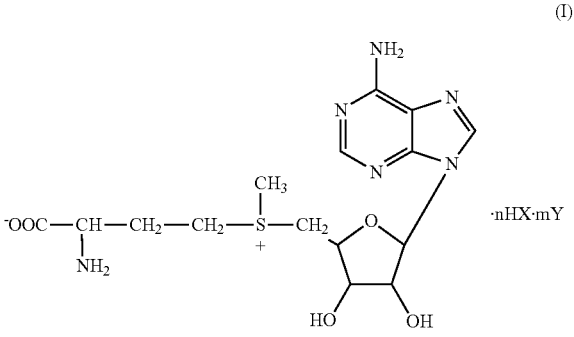

wherein
HX is a strong mineral acid having an acid dissociation constant (pKa) of less than 2.5 selected from the group consisting of hydrochloric acid, sulphuric acid, phosphoric acid, phosphorous acid, disulphonic acid and 1,4 butanedisulphonic acid;

n and m are independently a number in the range of 0.5-2.0; and

Y is selected from the group consisting of calcium oxide, magnesium oxide, calcium chloride, magnesium chloride, calcium sulphate, magnesium sulphate and mixtures thereof.

2. Salt according to claim 1, wherein Y is magnesium chloride.

3. Salt according to claim 1, wherein Y is calcium chloride.

4. Salt according to claim 1 in the form of oval or spherical particles.

5. Salt according to claim 1 having particle size in the range of 20-500 μm.

6. Salt according to claim 5, having particle size in the range of 50-300 μm.

7. Salt according to claim 1, comprising at least 70% by weight of SAMe.

8. Salt according to claim 2 in the form of oval or spherical particles.

9. Salt according to claim 3 in the form of oval or spherical particles.

10. Salt according to claim 2 having particle size in the range of 20-500 μm.

11. Salt according to claim 3 having particle size in the range of 20-500 μm.

12. Salt according to claim 4 having particle size in the range of 20-500 μm.

13. Salt according to claim 2, comprising at least 70% by weight of SAMe.

14. Salt according to claim 3, comprising at least 70% by weight of SAMe.

15. Salt according to claim 4, comprising at least 70% by weight of SAMe.

16. Salt according to claim 5, comprising at least 70% by weight of SAMe.

17. Method of using a medicament containing a salt of S-adenosylmethionine (SAMe) of formula (I) for the treatment of depressive states, wherein formula (I) comprises:

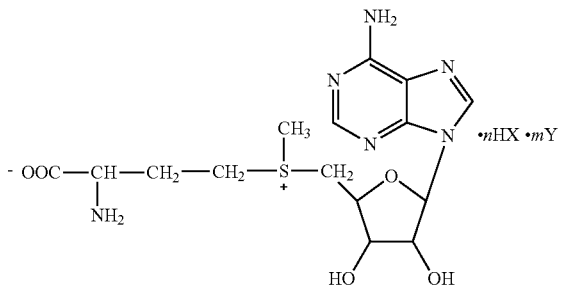

wherein
HX is a strong mineral acid having an acid dissociation constant (pKa) of less than 2.5 selected from the group consisting of hydrochloric acid, sulphuric acid, phosphoric acid, phosphorous acid, disulphonic acid and 1,4 butanedisulphonic acid;

n and m are independently a number in the range of 0.5-2.0; and

Y is selected from the group consisting of calcium oxide, magnesium oxide, calcium chloride, magnesium chloride, calcium sulphate, magnesium sulphate and mixtures thereof.

18. Salt according to claim 7, comprising from 75 to 90% by weight of SAMe.

19. Salt according to claim 13, comprising from 75 to 90% by weight of SAMe.

20. Salt according to claim 14, comprising from 75 to 90% by weight of SAMe.

21. Salt according to claim 15, comprising from 75 to 90% by weight of SAMe.

22. Salt according to claim 16, comprising from 75 to 90% by weight of SAMe.

* * * * *